United States Patent [19]

Giovanetto

[11] Patent Number: 4,892,938

[45] Date of Patent: Jan. 9, 1990

[54] METHOD FOR THE RECOVERY OF STEVIOSIDES FROM PLANT RAW MATERIAL

[76] Inventor: Roger H. Giovanetto, 2220 39 Avenue NE, T2E6P7 Calgary, Alberta, Canada

[21] Appl. No.: 221,811

[22] Filed: Jul. 20, 1988

[30] Foreign Application Priority Data

Jul. 21, 1987 [EP] European Pat. Off. ......... 87110541.7

[51] Int. Cl.$^4$ .......................... C07G 3/00; C07H 1/06
[52] U.S. Cl. .................................. 536/18.5; 536/128; 536/127
[58] Field of Search ....................... 536/6.3, 18.5, 128, 536/127

[56] References Cited

U.S. PATENT DOCUMENTS

| | | | |
|---|---|---|---|
| 4,361,697 | 11/1982 | Dobberstein et al. | 536/128 |
| 4,599,403 | 7/1986 | Kumar | 536/18.5 |

FOREIGN PATENT DOCUMENTS

| | | |
|---|---|---|
| 6191300 | 8/1976 | Japan. |
| 61149300 | 12/1976 | Japan. |
| 625800 | 1/1977 | Japan. |
| 62100500 | 8/1977 | Japan. |
| 62120170 | 10/1977 | Japan. |
| 63113065 | 10/1978 | Japan. |
| 6412400 | 1/1979 | Japan. |
| 65111768 | 8/1980 | Japan. |
| 65162953 | 12/1980 | Japan. |
| 66137866 | 10/1981 | Japan. |
| 6942862 | 3/1984 | Japan. |

*Primary Examiner*—Ronald W. Griffin
*Assistant Examiner*—Everett White
*Attorney, Agent, or Firm*—Jordan and Hamburg

[57] ABSTRACT

The invention relates to a method for recovering steviosides from dried plant material of Stevia rebaudiana Bertoni by extraction and purification. An extract is obtained through treatment in water at a temperature from room temperature to about 65° C. with stirring and subsequent filtration and centrifugation. This extract is treated with calcium hydroxide, whereupon a precipitate is obtained by means of filtration or centrifugation. This precipitate is treated with a strongly acidic ion exchange resin and subsequently with a weakly basic ion exchange resin, filtered and dried.

15 Claims, No Drawings

METHOD FOR THE RECOVERY OF STEVIOSIDES FROM PLANT RAW MATERIAL

BACKGROUND OF THE INVENTION

The invention is directed to a method for the recovery of steviosides from dried plant raw material of Stevia rebaudiana Bertoni by extraction and purification, undersirable impurities being removed by chemical treatment and the purification being accomplished with anionic and cationic exchange resins.

Steviosides are used as serviceable artificial sweeteners and are added to low-calorie foods or as replacement for natural sugar. Artificial sweeteners were developed for use by diabetics and to decrease the calorie content of food preparations, especially for a low-calorie diet. These sweeteners are frequently sweeter than natural sugar and may, in order to achieve the same measure of sweetening action, be used in small amounts. Numerous sweeteners are synthetic in nature, for example, saccharin, cyclamates and aspartames. The use of some of these is prohibited or limited, because pharmacological investigations have shown that they can produce cancer. On the ohter hand, the steviosides are fully usable and have shown no disadvantageous effects in clinical trials.

Conventional methods for the extraction and purification of steviosides are associated almost exclusively with the use of organic solvents, such as methanol, ethanol or ether, and many require that the steviosides be absorbed at first on a resin with subsequent elution with an organic solvent. The concentrated, evaporated solutions from this method usually are treated with methanol or ethanol to bring about the final crystallization of the end mixture. Other methods make use of iron or aluminum salts to remove impurities. These two materials require a further treatment with sodium hydroxide to remove residues of the iron or aluminum salts.

SUMMARY OF THE INVENTION

The invention seeks to simplify these methods, especially in order to lower the costs and to achieve better results. In the inventive method, the only chemical additive is calcium hydroxide, which is added to the starting material to remove unwanted impurities and coloring materials from the mass. All further steps of the method are carried out with water as solvent and the product is obtained by evaporating the water and drying to provide a stevioside of high purity, good taste and a satisfactory coloration, as well as in high total yield in relation to the raw material. The invention consists therein that, in a method of the initially described type through treatment in water at temperatures between room temperature and 65° C. and with stirring as well as subsequent filtration or centrifugation, an extract is obtained and that this extract is treated with $Ca(OH)_2$, whereupon by means of filtration and centrifugation a precipitate is obtained and treated with a strongly acidic ion exchange resin and subsequently with a weakly basic ion exchange resin, filtered and dried. As acidic ion exchanges, the resins known under the trade names of Dowex 50 W and Rohm and Haas IRA 120 or resins of similar activity come into consideration. The basic ion exchange resins may, for example, be the resins known under the trade names of Dowex WGR, Dowex MWA-1, Rohm and Haas IR4B or Rohm and Haas IRA93 or resins of similar activity. The solution is passed through a fine filter system and a sample is evaporated to determine the purity and quality. Corresponding to the desired purity and quality of the end product, this method, including the use of the strongly acidic ion exchange resin and of the weakly basic ion exchange resin, may be repeated several times, generally up to three times. The solution is then concentrated and filtered. The filtrate is dried and is obtained as a white powder, which contains about 75% stevioside compounds.

DETAILED DESCRIPTION OF THE PREFERRED EMBODIMENTS

It is within the scope of the invention that the extract is treated with calcium oxide, calcium carbonate or other basic calcium salts to form the precipitate. The treatment of the extract with basic salts of magnesium or aluminum forms a different alternative to this. Advantageously, the basic salts are added to the water during the extraction and with stirring.

Finally, the invention provides that, after the treatment with the strongly acidic ion exchange resin and a weakly basic ion exchange resin, the filtrate obtained is treated with a strongly acidic ion exchange resin as well as subsequently with a strongly basic ion exchange resin and that the solution obtained is concentrated, filtered and dried.

The inventive method is described in greater detail by means of the following examples.

EXAMPLE 1

The raw material, which contains the steviosides, is obtained by water extracting from a kilogram of plant material at temperatures of the order of room temperature to 65° C. Without additional concentration, this extract is treated with calcium hydroxide, in order to remove a number of unwanted plant components, and the whole is filtered in a fine filter system. The result is a clear solution, which contains 279 g of crude steviosides. This clear solution is then treated with a strongly acidic ion exchange resin, such as Dowex 50W, and the eluate obtained is then treated with a weakly basic ion exchange resin, such as Dowex WGR or the like. The eluate from this tratement if filtered through a fine filter medium before the next step of the process. The sequence of treatments with strongly acidic and weakly basic resins is repeated until a satisfactory product is obtained. This may extend from one to five treatments. After the elution and filtration at the end of the last ion exchanger treatment, the eluate obtained is concentrated and filtered in a fine filter system. The filtrate is dried and yields a purified product with 107 grams of steviosides with a purity of about 75%.

EXAMPLE 2

This method essentially corresponds to that of Example 1. However, after three consecutive treatemnts with a strongly acidic resin and a weakly basic resin and filtration, the eluate is concentrated. The concentrate is then treated once more with an appropriate strongly acidic resin and subsequently with a strongly basic resin. such as Dowex 2-X or Rohm and Hass IRA410 or the like. The product of this treatment is then concentrated and the concentrate filtered in a fine filter system. The end procuts, 102 g of a purified material, is obtained by drying. It contains steviosides, which have a purity of about 75%, but are less bitter in taste tests.

I claim:

1. A method for recovering steviosides from dried plant material of *Stevia rebaudiana* Bertoni, comprising treating dried plant material of *Stevia rebaudiana* Bertoni by stirring in a solvent consisting of water at a temperature ranging from room temperature to about 65° C., filtering or centrifuging the treated plant material to obtain an aqueous extract, treating the aqueous extract with calcium hydroxide to form a precipitate, filtering and centrifuging the treated extract to separate the precipitate, sequentially treating the separated precipitate three times, first with a strongly acidic ion exchange resin and then with a weakly basic ion exchange resin, and thereafter filtering and drying the treated precipitate to obtain a product containing steviosides without employing any solvents other than water.

2. A method as in claim 1, further comprising sequentially treating the separated precipitate with a strongly acidic ion exchange resin and a weakly basic ion exchange resin up to five times before filtering and drying to obtain the product containing steviosides.

3. A method as in claim 1, wherein the dried plant material is simultaneously stirred in water and treated with calcium hydroxide.

4. A method as in claim 1, further comprising, after said sequential treatment with said strongly acidic and weakly basic ion exchange resins, further treating the precipitate with a strongly acidic ion exchange resin, further treating the precipitate with a strongly basic ion exchange resin, and concentrating the treated precipitate prior to filtering and drying.

5. A method as in claim 1, wherein the treatments with said strongly acidic ion exchange resin and weakly basic ion exchange resin are intermittent.

6. A method for recovering steviosides from dried plant material of *Stevia rebaudiana* Bertoni, comprising treating dried plant material of *Stevia rebaudiana* Bertoni by stirring in a solvent consisting of water at a temperature ranging from room temperature to about 65° C., filtering or centrifuging the treated plant material to obtain an aqueous extract, treating the aqueous extract with a salt selected from the group consisting of calcium oxide, calcium carbonate and other basic calcium salts to form a precipitate, filtering and centrifuging the treated extract to separate the precipitate, sequentially treating the separated precipitates three times, first with a strongly acidic ion exchange resin and then with a weakly basic ion exchange resin, and thereafter filtering and drying the treated precipitate to obtain a product containing steviosides without employing any solvents other than water.

7. A method as in claim 6, further comprising sequentially treating the separated precipitate with a strongly acidic ion exchange resin and a weakly basic ion exchange resin up to five times before filtering and drying to obtain the product containing steviosides.

8. A method as in claim 6, wherein the dried plant material is simultaneously stirred in water and treated with said salt.

9. A method as in claim 6, further comprising, after said sequential treatment with said strongly acidic and weakly basic ion exchange resins, further treating the precipitate with a strongly acidic ion exchange resin, further treating the precipitate with a strongly basic ion exchange resin, and concentrating the treated precipitate prior to filtering and drying.

10. A method as in claim 6, wherein the treatments with said strongly acidic ion exchange resin and weakly basic ion exchange resin are intermittent.

11. A method of recovering steviosides from dried plant material of *Stevia rebaudiana* Bertoni, comprising treating dried plant material of *Stevia rebaudiana* Bertoni by stirring in a solvent consisting of water at a temperature ranging from room temperature to about 65° C., filtering or centrifuging the treated plant material to obtain an aqueous extract, treating the aqueous extract with a salt selected from the group consisting of basic magnesium salts and basic aluminum salts to form a precipitate, filtering and centrifuging the treated extract to separate the precipitate, sequentially treating the separated precipitate three times, first with a strongly acidic ion exchange resin and then with a weakly basic ion exchange resin, and thereafter filtering and drying the treated precipitate to obtain a product containing steviosides without employing any solvents other than water.

12. A method as in claim 11, further comprising sequentially treating the separated precipitate with a strongly acidic ion exchange resin and a weakly basic ion exchange resin up to five times before filtering and drying to obtain the product containing steviosides.

13. A method as in claim 11, wherein the dried plant material is simultaneously stirred in water and treated with said salt.

14. A method as in claim 11, further comprising, after said sequential treatment with said strongly acidic and weakly basic ion exchange resins, further treating the precipitate with a strongly acidic ion exchange resin, further treating the precipitate with a strongly basic ion exchange resin, and concentrating the treated precipitate prior to filtering and drying.

15. A method as in claim 11, wherein the treatments with said strongly acidic ion exchange resin and weakly basic ion exchange resin are intermittent.

* * * * *